US00PP37658P2

(12) United States Plant Patent
Juist

(10) Patent No.: US PP37,658 P2
(45) Date of Patent: Sep. 1, 2026

(54) ***LITHODORA* PLANT NAMED 'LTHZ0001'**

(50) Latin Name: *Lithodora diffusa*
Varietal Denomination: LTHZ0001

(71) Applicant: SYNGENTA CROP PROTECTION AG, Basel (CH)

(72) Inventor: Monique Juist, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/062,093

(22) Filed: Feb. 25, 2025

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
CPC ..... A01H 5/02; A01H 5/00; A01H 6/00
See application file for complete search history.

(56) References Cited

PUBLICATIONS

Syngenta Flowers Wholesale Catalogue 2025 Cuttings, retrieved on Jul. 29, 2025 at https://online.flippingbook.com/view/90219826/, pp. 1-5, 124 (4 pp. total). (Year: 2025).*
YouTube Video Syngenta Flowers Lithodora Tidepool 2024, retrieved on Jul. 29, 2025 at https://www.youtube.com/watch?v= X5CQwTgsoZs, 2 pp. (Year: 2024).*
Syngenta Flowers Wholesale Catablogue 2025 Cuttings, retrieved on Jul. 29, 25 at https://online.flippingbook.com/view/90219826/, pp . 1-5, 124. (Year: 2025).*
YouTube Video Syngenta Flowers Lithodora Tidepool 2024, retrieved on Jul. 29, 25 at https://www.youtube.com/watch?v= X5CQwTgsoZs, 2 pp. (Year: 2024).*

* cited by examiner

*Primary Examiner* — June Hwu
(74) *Attorney, Agent, or Firm* — Dale Skalla

(57) ABSTRACT

A new *Lithodora* plant named 'LTHZ0001' particularly distinguished by its medium sized flowers, a dense branching plant, a blue flower color, medium early flowering, and a semi trailing to mounding plant habit.

1 Drawing Sheet

Latin name of the genus and species of the plant claimed: *Lithodora diffusa.*

Varietal denomination: 'LTHZ0001'.

BACKGROUND OF THE NEW PLANT

The present invention comprises a new *Lithodora*, botanically known as *Lithodora diffusa*, and hereinafter referred to by the variety name 'LTHZ0001'.

'LTHZ0001' is a product of a planned breeding program. The new cultivar has medium sized flowers, a dense branching plant, a blue flower color, medium early flowering, and a semi trailing to mounding plant habit.

'LTHZ0001' originated from a hybridization made in April 2015 in a controlled breeding environment in Enkhuizen, The Netherlands. The female parent was the proprietary selection 'J6656-1V'. Compared to 'LTHZ0001', it is less vigorous, has a lighter blue flower color, is earlier flowering and has a more trailing plant habit.

The male parent of 'LTHZ0001' was the proprietary selection 'J6657-1V'; a plant with very small flowers purple to blue flower color, somewhat less vigorous and with a similar plant habit.

The resulting seeds were sown in August 2015. 'LTHZ0001' was selected as one flowering plant within the progeny of the stated cross in March 2016 in a controlled environment in Enkhuizen, The Netherlands.

The first act of asexual reproduction of 'LTHZ0001' was accomplished when vegetative cuttings were propagated from the initial selection in March 2016 in a controlled environment in Enkhuizen, The Netherlands.

BRIEF SUMMARY OF INVENTION

Horticultural examination of plants grown from cuttings of the plant initiated in March 2016 and continuing thereafter, has demonstrated that the combination of characteristics as herein disclosed for 'LTHZ0001' are firmly fixed and are retained through successive generations of asexual reproduction.

'LTHZ0001' has not been observed under all possible environmental conditions. The phenotype may vary significantly with variations in environment such as temperature, light intensity, and day length.

A Plant Breeder's Right for this cultivar has not yet been applied for. 'LTHZ0001' has not been made publicly available prior to the effective filing date of this application, notwithstanding any disclosure that may have been made less than one year prior to the effective filing date of this application by the inventor or another who obtained 'LTHZ0001' directly from the inventor.

The following traits have been repeatedly observed and are determined to be basic characteristics of the new variety. The combination of these characteristics distinguishes this *Lithodora* as a new and distinct variety.

BRIEF DESCRIPTION OF THE PHOTOGRAPHS

The accompanying photographic drawing shows typical flower and foliage characteristics of 'LTHZ0001' with colors being as true as possible with an illustration of this type.

Figure 1:
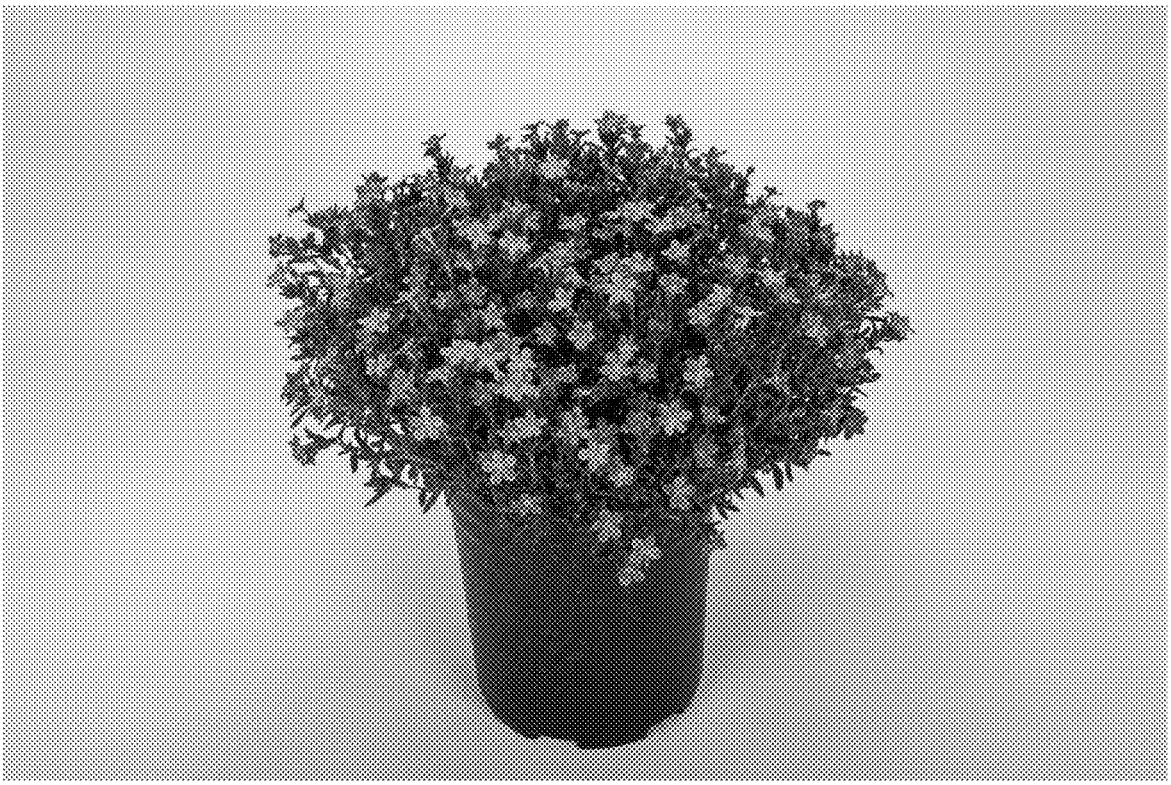
Figure 2:
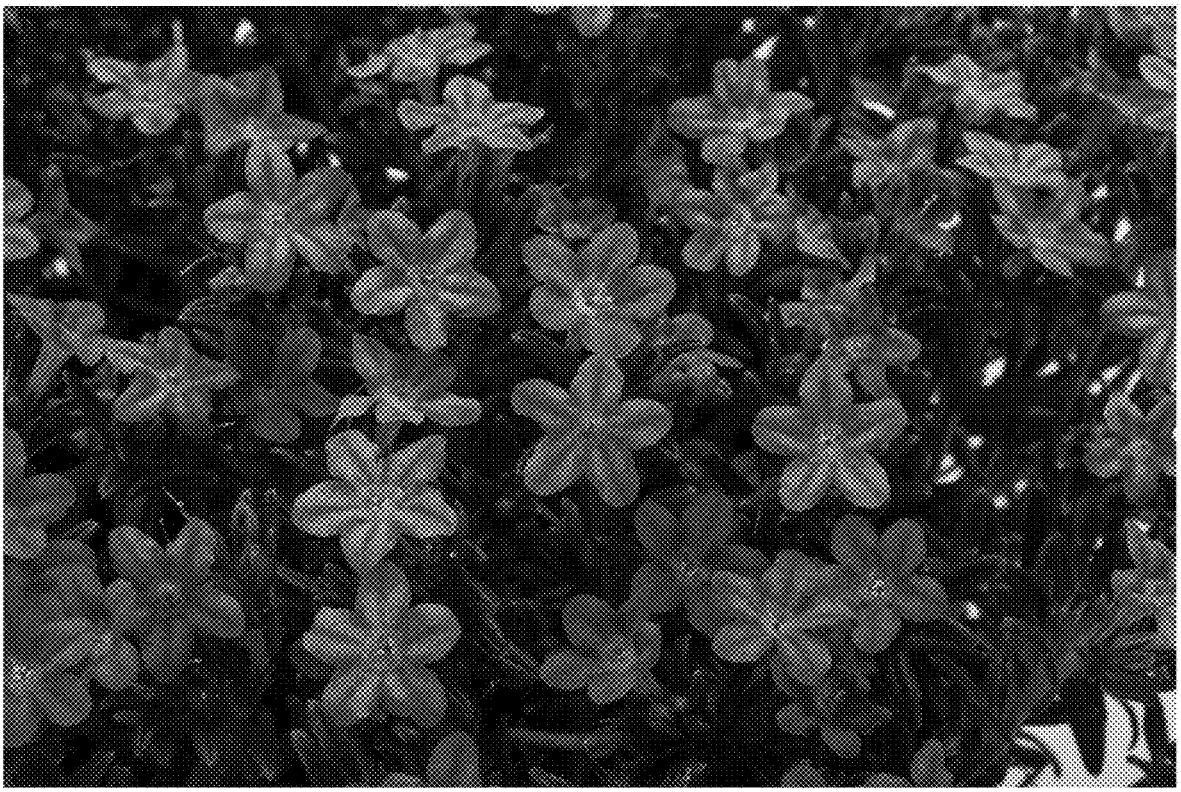

The photographic drawing shows in
FIG. 1 a flowering plant of the new variety and in
FIG. 2 a close-up of the flowers.

DETAILED BOTANICAL DESCRIPTION

The aforementioned photographs were taken on Apr. 5, 2021 from plants growing indoor in 14 cm pots in Enkhuizen, The Netherlands. These plants were approximately 25 weeks of age.

The plant descriptions and measurements were taken in December 2024 in Enkhuizen, The Netherlands on plants grown in 12.5 cm pots. These plants were about 16 weeks old.

Color references are made to The Royal Horticultural Society Colour Chart (R.H.S.) 2001.

TABLE 1

DIFFERENCES BETWEEN THE NEW VARIETY 'LTHZ0001' AND A SIMILAR VARIETY

| | 'LTHZ0001' | 'Grace Ward', Not patented |
|---|---|---|
| Earliness: | Medium early | Early to very early |
| Plant habit: | Semi trailing to mounding | Trailing |
| Branching: | Excellent branching | Medium branching |

Plant:
- *Form, growth and habit.*—Semi trailing to mounding plant habit.
- *Plant height.*—12 cm.
- *Plant height* (*inflorescence included*).—13 cm.
- *Plant diameter* (*width*).—Approximately 23 cm.

Roots:
- *Number of days to initiate and produce roots.*—14 days at about 22° C.
- *Type.*—Fine, fibrous, free branching.
- *Color.*—RHS N158D.

Foliage:
- *Arrangement.*—Alternate, simple.
- *Immature leaf, color upper surface.*—RHS 137B.
- *Immature leaf, color lower surface.*—RHS 138B.
- *Mature leaf, color upper surface.*—RHS 139A.
- *Mature leaf, color lower surface.*—RHS 137D.
- *Length.*—2.5 cm.
- *Width.*—0.7 cm.
- *Shape.*—Ensiform.
- *Apex shape.*—Acute.
- *Margin.*—Moderately revolute, entire.
- *Texture, upper surface.*—Densely covered with short hairs.
- *Lower surface.*—Densely covered with short hairs.
- *Color of veins, upper surface.*—RHS 145A.
- *Color of veins, lower surface.*—RHS 145A.
- *Petiole.*—No petiole present.

Stem:
- *Quantity of main branches per plant.*—8-9.
- *Color of stem.*—RHS 145A.
- *Length of stem.*—11 cm.
- *Diameter.*—0.3 cm.
- *Length of internodes.*—0.4-1.2 cm.
- *Texture.*—Densely covered with short hairs.
- *Color of pedicel.*—RHS 145A.
- *Length of pedicel.*—0.2-0.3 cm.
- *Diameter of pedicel.*—0.2 cm.
- *Texture of pedicel.*—Densely covered with short hairs.

Inflorescence:
- *Type.* Terminal cyme, 3-5 flowers per cyme, flowering time early April to mid May (in Andijk, The Netherlands).
- *Inflorescence size.*—2.5 cm wide, 3 cm long.
- *Lastingness of individual blooms on the plant.*—About 5 days.
- *Fragrance.*—No smell.

Bud (just when opening):
- *Color.*—RHS N87B at top, RHS N82C towards base.
- *Length.*—1.4 cm.
- *Width.*—0.4 cm.
- *Shape.*—Obovate.

Mature flower:
- *Corolla description.*—5 lobed, each lobe 7 mm long and 4 mm wide, fused at base.
- *Flower horizontal diameter.*—1.8 cm.
- *Flower height* (*vertical*).—1.4 cm.
- *Color upper surface.*—RHS 101A.
- *Color lower surface.*—RHS 101A towards margin, RHS 101B towards tube.
- *Conspicuousness of veins.*—Rather strong.
- *Color of veins.*—RHS 83B (lower surface), RHS N109A (upper surface).
- *Apex shape.*—Rounded.
- *Margin.*—Entire.
- *Petal texture, upper surface.*—A few hairs, but near corolla tube dense, up to 1 mm long hairs.
- *Petal texture, lower surface.*—Pubescent.
- *Corolla tube color outside.*—RHS N89B near corolla, RHS N79D in middle, RHS 157C towards ovary.
- *Corolla tube color inside.*—RHS 83A near corolla, RHS 158B near ovary.
- *Conspicuousness of veins in tube.* Medium.
- *Corolla tube length.*—1.0 cm.
- *Corolla tube texture, outside.*—Pubescent.
- *Corolla tube texture, inside.*—Glabrous.

Calyx:
- *Color of sepal, upper surface.*—RHS 138A.
- *Color of sepal, lower surface.*—RHS 138A.
- *Length.*—0.6 cm.
- *Width.*—0.2 cm.
- *Shape.*—Linear.
- *Apex shape.*—Acute.
- *Base.*—Fused.
- *Margins.*—Entire.
- *Texture, upper surface.*—Densely covered with short hairs.
- *Lower surface.*—Densely covered with short hairs.

Reproductive organs:
- *Pistil.*—1.
- *Length.*—1.4 cm.
- *Style color.*—RHS 157D.
- *Style length.*—1.1 cm.
- *Stigma color.*—RHS 145D.
- *Ovary shape and color.*—4 lobed, RHS 145D.
- *Ovary size.*—1 mm wide, 2 mm long.
- *Stamens.*—
- *Quantity per flower.*—5.
- *Color of filaments.*—RHS 187B.
- *Length filaments.*—0.7 cm.
- *Anther color.*—RHS 1D.
- *Anther length.*—0.1 cm.

*Anther shape.*—Elliptical.
*Color of pollen.*—RHS 18C.
*Pollen amount.*—Abundant.
*Fertility/seed set.*—Has not been observed on this hybrid to date.
*Disease/pest resistance.*—Has not been observed on this hybrid to date.

What is claimed is:

1. A new and distinct variety of *Lithodora* plant named 'LTHZ0001' substantially as illustrated and described herein.

* * * * *